United States Patent [19]

Katsumata et al.

[11] Patent Number: 4,558,458
[45] Date of Patent: Dec. 10, 1985

[54] POSITIONING UNIT FOR RADIATION TOMOGRAPHY APPARATUS

[75] Inventors: Kenichiro Katsumata, Otawara; Yasuo Nobuta, Tochigi, both of Japan

[73] Assignee: Tokyo Shibaura Denki Kabushiki Kaisha, Kawasaki, Japan

[21] Appl. No.: 559,011

[22] Filed: Dec. 8, 1983

Related U.S. Application Data

[63] Continuation of Ser. No. 513,786, Jul. 15, 1983, which is a continuation of Ser. No. 331,024, Dec. 15, 1981, abandoned.

[30] Foreign Application Priority Data

Dec. 17, 1980 [JP] Japan ............................. 55-178399

[51] Int. Cl.$^4$ ............................................ G03B 41/16
[52] U.S. Cl. ...................................... 378/20; 378/206
[58] Field of Search ................. 378/20, 177, 179, 180, 378/195, 196, 205, 206, 209

[56] References Cited

U.S. PATENT DOCUMENTS 4,024,403 5/1977 Bernstein .
4,117,337 9/1978 Staats .
4,181,858 1/1980 Moore .
4,211,927 7/1980 Hellstrom .
4,242,587 12/1980 Lescrenier .
4,296,329 10/1981 Mirabella .

Primary Examiner—Craig E. Church
Attorney, Agent, or Firm—Finnegan, Henderson, Farabow, Garrett & Dunner

[57] ABSTRACT

A positioning unit for a radiation tomography apparatus comprises light beam detector and a light beam generator which are disposed opposite to each other on a horizontal line passing through the center of a photographing region irradiated by X-rays, a table top on which a patient is laid, driving device for driving the table top in the vertical direction, position detector for outputting a signal whose magnitude corresponds to the position of the table top; and controller which obtains data corresponding to the distance from an upper surface of a part of body to be photographed of the patient to the horizontal line of the photographing region, based on an output signal of the light beam detector and an output signal of the position detector. The controller obtains distance data for aligning the horizontal line passing through the center of the photographing region with the center of the part of body to be photographed, in accordance with the distance data and data corresponding to the horizontal line, and it drives the driving device until a signal which corresponds to desired distance data is output from the position detector.

4 Claims, 10 Drawing Figures

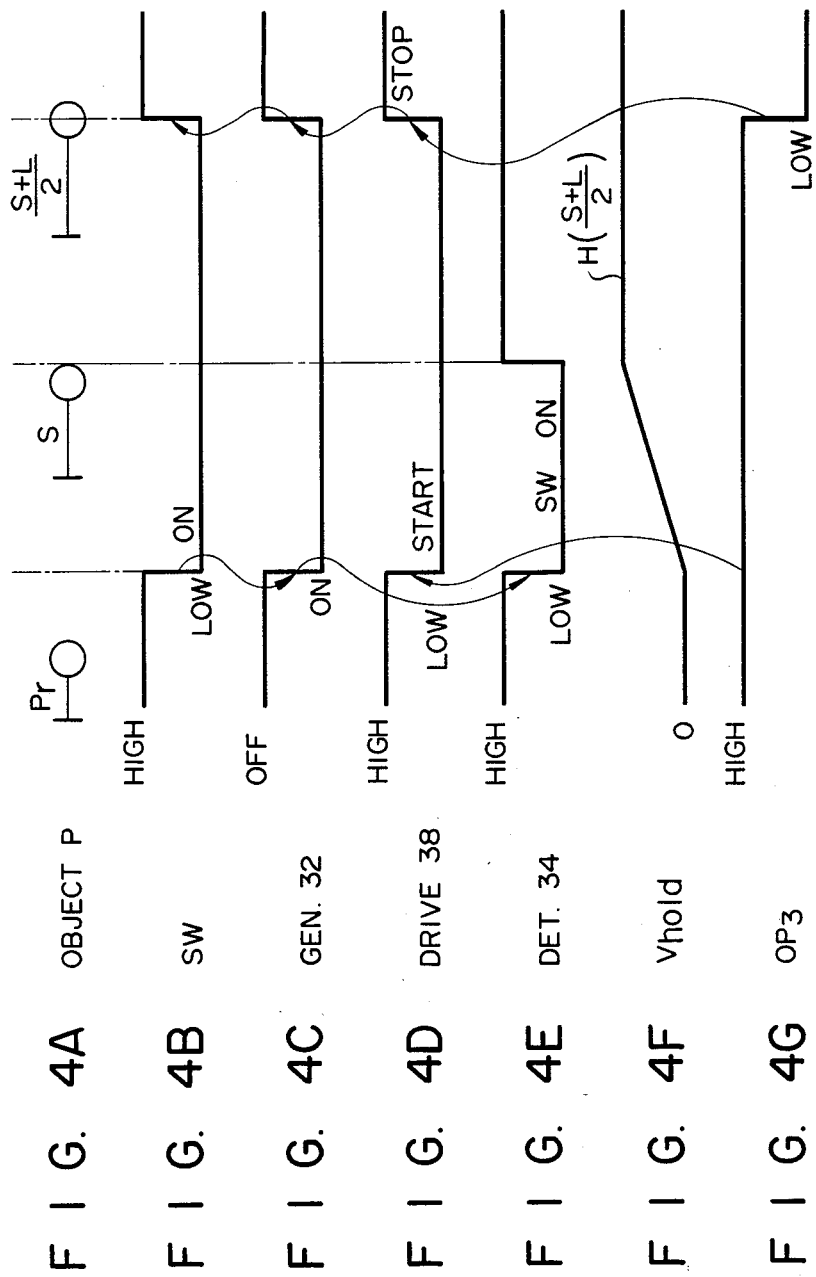

POSITIONING UNIT FOR RADIATION TOMOGRAPHY APPARATUS

This application is a continuation, of application Ser. No. 513,786, filed 7-15-83 Ser. No. 513,786 is a continuation of Ser. No. 331,024, filed 12/15/81 abandoned.

BACKGROUND OF THE INVENTION

The present invention relates to a positioning unit for a radiation tomography apparatus in which a patient is so positioned that the part of body to be photographed may lie at a desired position.

Conventionally, a computerized tomography apparatus (to be referred to as a CT apparatus hereinafter) is known as one of the radiation tomography devices. The CT apparatus comprises an X-ray source 12 which radiates a flat, sector-shaped X-ray beam (fan beam X-ray) FX in a pulse-generating manner, a table 14 on which a patient P is laid, and a radiation detector 16 which opposes the X-ray source 12 with the table top 14 interposed. The radiation detector 16 is constituted by a plurality of radiation detecting elements D1, D2, ..., Dm, ..., Dn which are aligned parallel to each other, as shown in FIG. 1. In use of the unit of the tomography apparatus, a patient P is laid on the table 14, and the X-ray source 12 and the radiation detector 16 rotate periodically in the same circumferential direction through a predetermined angle about a part of body to be photographed of the patient P. With each rotation, X-rays radiated from the X-ray source 12 and transmitted through the patient P are detected by the radiation detector 16. Detection data for each exposure to the X-rays is collected and the obtained detection data is processed by a computer. The resultant data obtained by the computer processing are reconstructed to obtain a tomogram of the plane to be photographed. A zone 18 surrounded by the broken lines in the figure is a photographing region which is formed by the X-ray source 12 and the radiation detector 16.

In a CT apparatus, the part of body to be photographed of the patient P must overlap the photographing region (the region in which all the beams FX radiated from the X-ray source overlap, each time the X-ray source 12 and the radiation detector 16 are shifted by a predetermined angle). However, the photographing region cannot be visually observed. It is, therefore, difficult to match the plane to be photographed with the photographing region. In order to obtain a tomogram with higher precision, it is desired that a patient is so positioned that the part of body to be photographed lies at the center of the photographing region. However, this kind of positioning requires higher precision, resulting in more difficulty.

Conventional positioning units are classified into two types. A first kind of positioning unit adopts a system which uses a projector or phantom and in which the operator estimates the position of the patient with his eyes. A second kind of positioning unit adopts a system for accomplishing positioning by a microcomputer.

Among the conventional positioning units, units for positioning by a projector or a phantom require visual estimation for positioning the patient within the photographing region. Therefore, the positioning error may become great. Further, in devices of these types, the table top is manually moved upward or downward, requiring much labor. On the other hand, in the device for achieving positioning by a microcomputer, the operating cost is high and input data for the size of the patient is also required, resulting in time consuming operation.

None of the conventional positioning units satisfy all the requirements from the points of view of positioning precision, operability and operating cost.

SUMMARY OF THE INVENTION

The present invention has been made in consideration of this and has for its object to provide a positioning unit for a computerized tomography apparatus, which is flexible in operation in which operating cost is low, and in which high precision positioning is performed.

In order to achieve the above and other objects of the present invention, there is provided a positioning unit for a radiation tomography apparatus, said positioning unit comprising light beam detection means and a light beam generator which are disposed opposite to each other on a horizontal line passing through the center of a photographing region irradiated by X-rays; a table top on which an object is laid; driving means for lifting and lowering said table top; position detection means for outputting a signal whose magnitude corresponds to the position of said table top; and controller means which obtains distance data corresponding to the distance from an upper surface of a part of the body to be photographed of the object to said horizontal line of said photographing region, based on an output signal of said light beam detection means and an output signal of said position detection means, which obtains distance data necessary for aligning said horizontal line of said photographing region with the center of the part of body to be photographed, from the distance data and data corresponding to said horizontal line, and which drives said driving means until an output which corresponds to the distance data is obtained from said position detection means.

BRIEF DESCRIPTION OF THE DRAWINGS

FIGS. 4A to 4G show timing charts for explaining the mode of operation of the controller shown in FIG. 3.

DETAILED DESCRIPTION OF THE PREFERRED EMBODIMENTS

The preferred embodiments of the present invention will now be described with reference to the accompanying drawings.

Figure 1:
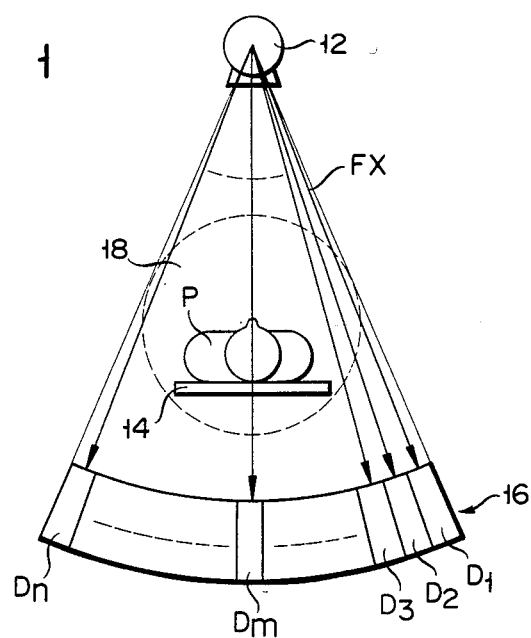
FIG. 1 is a view for illustrating a process for obtaining a tomogram in computerized tomography.
Figure 2:
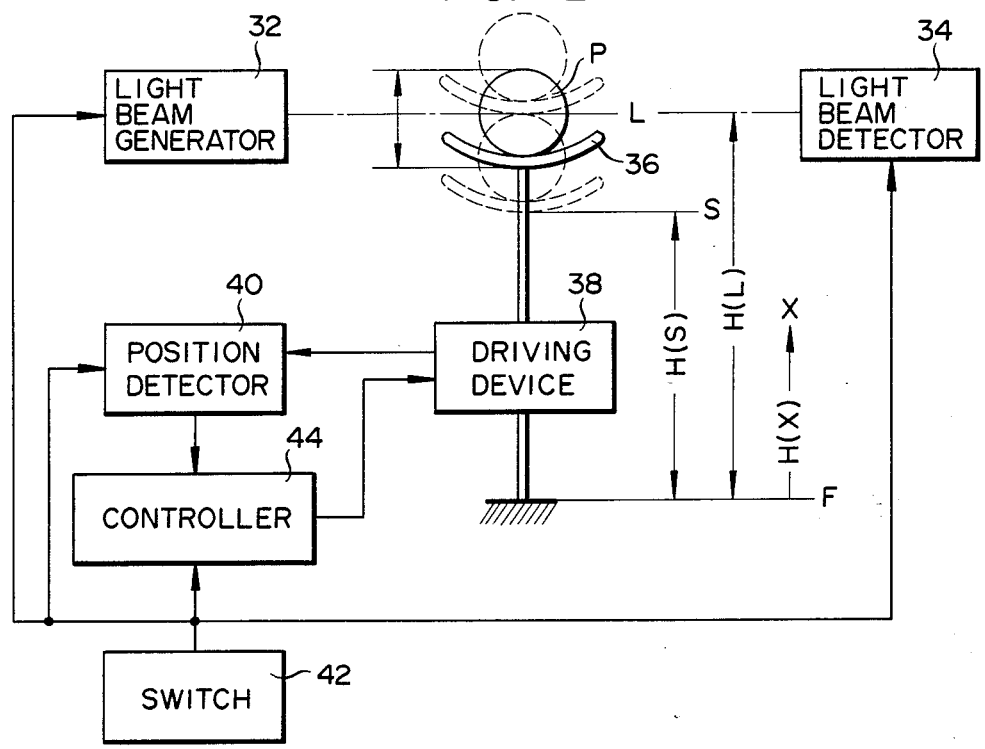
FIG. 2 is a block diagram of one embodiment of a positioning unit according to the present invention.

FIG. 2 shows a block diagram of a positioning unit according to the present invention.

Referring to FIG. 2, reference numeral 32 denotes a light beam generator, and reference numeral 34 denotes a light beam detector which are arranged on a horizontal line passing the center of a photographing region, the photography region being defined by a radiation source (not shown) disposed within a photographing hole in a gantry (not shown) and a radiation detector (not shown). The light beam detector 34 opposes the light beam generator 32 with the photographing region interposed therebetween. An object, for example a patient P, is laid on a table top 36. A driving device 38 drives the table top 36 in the vertical direction. A position detector 40 detects the position of the table top 36 which is driven by the driving device 38 in the vertical direction. When a system operation switch 42 is turned on, it supplies a start command to the light beam generator 32, the light beam detector 34, the position detector 40 and a controller 44 to set the system in the operative condition. Based on an output signal from the position detector 40 and an output signal from the light beam detector 34, the controller 44 controls the operation of the driving device 38 to arrange the center of a part of body to be photographed of the patient P laid on the table at a position "L" on the central horizontal line of the photographing region.

The mode of operation of the positioning unit of the construction as described above will now be described.

The system operation switch 42 is first turned on to set the light beam generator 32, the light beam detector 34, the position detector 40, and the controller 44 under the operative condition. When placed under the operative condition, the controller 44 performs a predetermined operation according to the output signals from the position detector 40 and the light beam detector 34, and generates a control signal for controlling the driving condition of the driving device 38. The driving device 38 is controlled by the control signal from the controller 44 and raises, for example, the table top 36. As the table top 36 is moved upward, the patient P placed on the table top 36 is also moved upward. When the upper end of the part of body to be photographed reaches the position "L" of the horizontal line passing the center of the photographing region, the optical path of the light emitted from the light beam generator 32 to the light beam detector 34 is blocked. Since no more light is incident on the light beam detector 34, the light beam detector 34 outputs a detection signal which represents the blockage of light, that is, detection of the patient P. This detection signal is input to the controller 44. The controller 44 stores the output signal from the light beam detector 34 when it receives the detection signal, that is, when the light emitted from the light beam generator 32 is blocked. The position detector 40 operates in cooperation with the driving device 38 and generates an output signal of a magnitude corresponding to the distance from the floor surface F to the table top 36, that is, a vertical position X. Therefore, when the vertical position of the table top 36 is represented by "S" at the instant of light blockage and the output signal from the position detector 40 at this instant is represented by H(S), the controller 44 stores the output signal of a magnitude equal to H(S).

The controller 44 also stores in advance H(L) which is an output signal of the position detector 40 and corresponds to the vertical position "L" of the central horizontal line L of the photographing region. The vertical position "L" is a fixed value regardless of the length in the vertical direction of the part of body of the patient P. Therefore, the controller 44 can store H(L) prior to the positioning operation of the patient P.

Based on data H(L) which is stored in advance and data H(S) which is stored at the instant of light blockage, the controller 44 obtains, according to relation (2) to be described later, data on a distance from the center of the part of body of the patient P to the center of the photographing region. The controller 44, based on the data thus obtained, drives the driving device 38 to move the table top 36 supporting the patient P upward by a distance corresponding to the distance data. The controller 44 stops driving the driving device 38 when a signal representing the position corresponding to the calculated distance data is obtained from the position detector 40. In this manner, the center of the part of body and the position "L" of the central horizontal line of the photographing region are aligned.

The principle of operation of the controller 44 will now be described.

Assume that the length in the vertical direction of the part of body to be photographed is l, and the thickness of the table top 36 is small enough to be negligible as compared with the length l. Then, a position at a distance by "l/2" (pl) above the position represented by "S" coincides with the point at which the position "L" of the central horizontal line of the photographing region is aligned with the center of the part of body. This position may be represented by $$L = S + l \tag{1}$$

On the other hand, the distance Pl from the center (in the vertical direction) of the part of body to the upper surface thereof may be given by $$Pl = l/2 = (L - S)/2 \tag{2}$$

Therefore, if the vertical position "L" which is a fixed value is given, and the vertical position "S" is obtained from the output signal H(S) from the position detector 40 upon reception of the detection signal representing light blockage, "Pl" may be obtained from relation (2). By moving the table top 36 upward by the distance "Pl", the center of the part of body may be aligned with the horizontal position at the center of the photographing region. In order to enhance the precision, the thickness of the table top 36 may be taken into consideration.

By substituting relation (2) in relation (1), the following relation (3) is obtained:

$$L = S + l/2 = S + (L - S)/2 = (S + L)/2 \tag{3}$$

Therefore, in practice, by moving the table top 36 upward until the output signal corresponding to $(S+L)/2$ represented by relation (3), that is, $H[(S+L)/2]$ is output from the position detector 40, the center of the part of body may be aligned with the horizontal position at the center of the photographing region.

Figure 3:
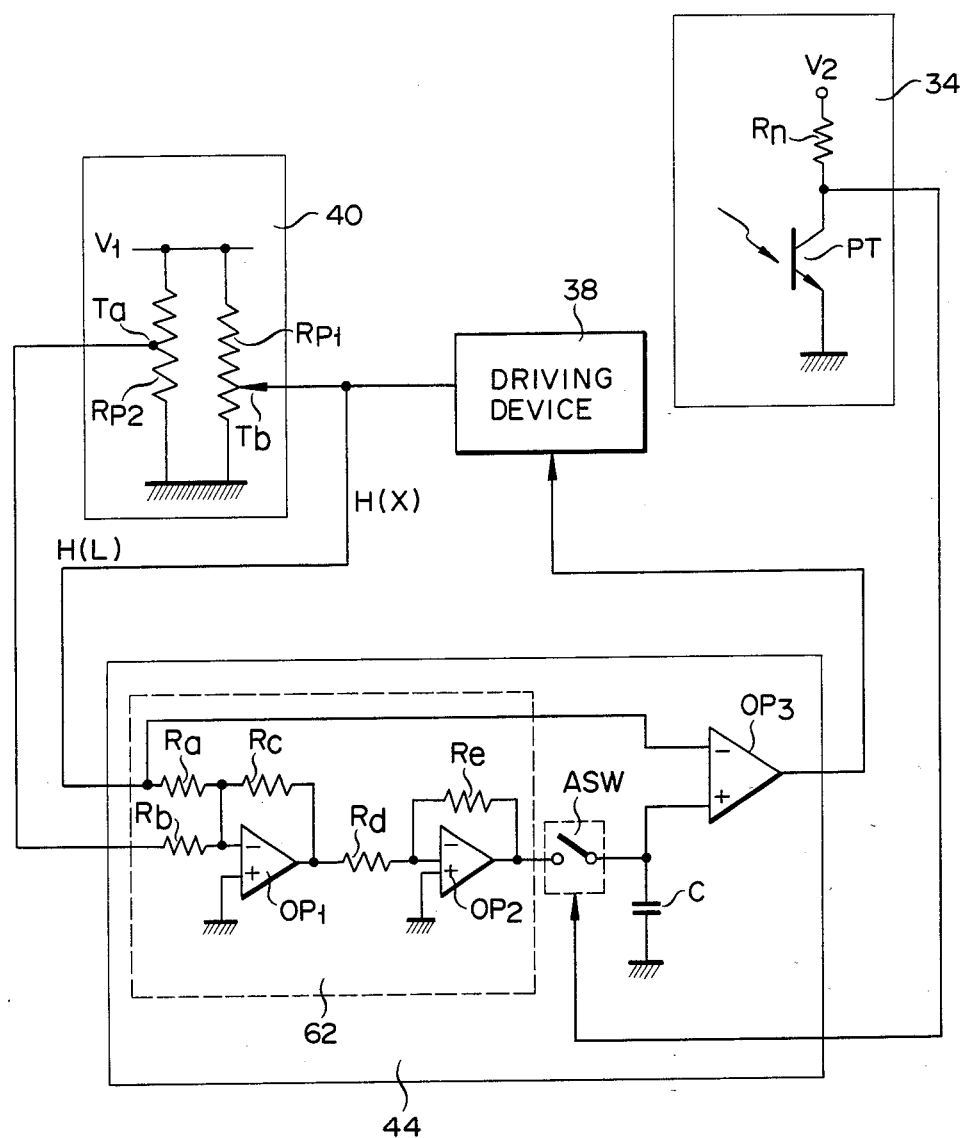
FIG. 3 is a detailed circuit diagram of a controller of the positioning unit shown in FIG. 2.

Although the controller 44 may comprise a microcomputer which digitally processes the signals, it may alternatively comprise one which processes signals in the analog manner, as shown in FIG. 3.

In the configuration of the controller 44 shown in FIG. 3 the position detector 40 ouputs an output H(L) of a magnitude corresponding to the position "L" which is a fixed value and an output H(X) of the magnitude corresponding to the vertical position "X" from the floor surface F in synchronism with the movement by the driving device 38. The position detector 40 comprises a pair of resistors Rp1 and Rp2, each having one end. connected to a power source at a suitable potential V1 and the other end connected to a reference potential, for example, ground. A stationary terminal Ta of the transistor Rp2 is connected to a resistor Rb of the controller 44. The potential at the terminal Ta with reference to the reference potential is set to correspond to a value which, in turn, corresponds to the position "L" in the apparatus shown in FIG. 2. Therefore, a constant potential H(L) corresponding to the position "L" is supplied to the resistor Rb of the controller 44. A movable terminal Tb of the resistor Rp1 is connected to the driving device 38 and a resistor Ra of the controller 44. The movable terminal Tb operates in synchronsim with the driving operation of the driving device 38, so that the output potential thereof is set at a value corresponding to the position of the table top 36. Therefore, a potential H(X) corresponding to the position of the table top 36 is supplied to the resistor Rb of the controller 44.

The light beam detector 34 may comprise, for example, a phototransistor PT. The collector of the phototransistor PT is connected to a power source at a suitable potential V2 as well as to an analog switch ASW of the controller 44. The emitter of the phototransistor PT is connected to a point of reference potential, for example, ground. When a light beam from the light beam generataor 32 is received, collector current flows in the phototransistor PT. Part of this collector current is input to the analog switch ASW to control it.

The system controller 44 has the configuration to be described below. The inverting input terminal (−) of an operational amplifier OP1 is connected to the terminal Tb of the position detector 40 through a resistor Ra for outputting H(X) and to the terminal Ta for outputting H(L). The non-inverting input terminal (+) of the operational amplifier OP1 is grounded. A feedback resistor Rc is connected between the output terminal and the inverting input terminal of the operational amplifier OP1. The resistance of the resistors Ra and Rb is "r1", and the resistance of the resistor Rc is "r1/2". Therefore, the operational amplifier OP1 produces an output signal of a magnitude which is half the magnitude of the composite signal of the output signals H(X) and H(L) from the position detector 40. The output terminal of the operational amplifier OP1 is also connected to the inverting input terminal (−) of an operational amplifier OP2 through a resistor Rd. A feedback resistor Re is connected between the inverting input terminal (−) and the output terminal of the operational amplifier OP2. The resistance of the resistors Rd and Re is "r2". The non-inverting input terminal (+) of the operational amplifier OP2 is grounded. Therefore, the operational amplifier OP2 serves to invert the output of the operational amplifier OP1.

The circuit consisting of the operational amplifiers OP1 and OP2 and the resistor Ra, Rb, Rc, Rd and Re functions as a comparator constituting an arithmetic circuit 62 for performing the operation of (S+L)/2 of relation (3).

The analog switch ASW is arranged at the output end of the operational amplifier OP2. The on/off operation of the analog switch ASW is controlled by an output signal from the light beam detector 34. In response to an output signal from the light beam detector 34 indicating reception of a light beam, the analog switch ASW is closed. In response to an output signal from the light beam detector 34 indicating absence of a light beam, the analog switch ASW is opened. The comparator OP3 comprises an operational amplifier. The non-inverting input terminal (+) of the comparator OP3 is connected to one end of a capacitor C, the other end of which is grounded and which accumulates a charge equivalent in potential to H(S+L/2) which corresponds to the vertical position "L". The non-inverting input terminal (+) of the comparator OP3 is also connected to the output end of the operational amplifier OP2 through the analog switch ASW. The inverting input termiinal (−) of the comparator OP3 is connected to the movable terminal Tb of the position detector 40 to receive the output signal H(X) as an input signal for comparison. The output terminal of the comparator OP3 is connected to the driving device 38, so that the output signal of the comparator OP3 may be applied to the driving device 38 as a control signal.

The mode of operation of the circuit of the configuration as shown in FIG. 3 will now be described with reference to FIGS. 4A to 4G, which are timing charts.

The initial conditions are as shown in FIG. 4A wherein the patient P is at the lowest position "Pr". When the system operation switch 42 is turned on, it outputs a start signal of low level as shown in FIG. 4B. Then, the light beam generator 32 is turned on as shown in FIG. 4C and produces a light beam. The light emitted from the light beam generator 32 becomes incident on the phototransistor constituting the light beam detector 34, which is rendered conductive. Upon reception of the light emitted from the light beam generator 32, the light beam detector 34 outputs a detection signal of low level as shown in FIG. 4E. This detection signal is supplied to the analog switch ASW of the controller 44 as a control signal. Upon reception of the detection signal of low level, the analog switch ASW is closed, and the output signal from the operation amplifier OP2 is input to the comparataor OP3. Since the table top 36 is at the lowest position "Pr", the position detector 40 produces the output H(L) which is a fixed value and the output H(Pr) of a magnitude corresponding to the lowest position. Therefore, both these outputs H(L) and H(Pr) are input to the operational amplifier OP1. The operational amplifier OP1 outputs a signal of −H[(Pr+L)/2] corresponding to −[(Pr+L)/2]. The output of the operational amplifier OP1 is input to the operational amplifier OP2 which inverts the input signal to provide an output H[(Pr+L)/2] corresponding to [(Pr+L)/2]. This is input to the non-inverting input terminal (+) of the comparator OP3. Since the capacitor C is connected between the non-inverting input terinal (+) of the comparator OP3 and ground, the charge corresponding to the output H[(Pr+L)/2] is accumulated on the capacitor C. A charge voltage $V_{hold}$ of the capacitor C due to this accumulation of charge is as shown in FIG. 4F. The output signal H(Pr) from the position detector 40 is input to the inverting input terminal (−) of the comparator OP3. Therefore, the comparator OP3 compares the output signal H(Pr) with the charge voltage $V_{hold}$ of the capacitor C as a reference.

Since the table top 36 is at the lowest position "Pr", in the controller 44 having the arithmetic circuit 62 wherein the operational amplifier OP1 amplifies the sum of the output signals from the position detector 40 with an amplification factor of −½ and the operational amplifier OP2 amplifies the output of the operational amplifier of with an amplification factor of −1, the signal H(Pr) is smaller than $V_{hold}$. Therefore, the comparator OP3 produces an output signal of high level as shown in FIG 4G, which represents the misalignment of the two positions. This signal of high level is input to the driving device 38 as a control signal for driving it. Therefore, the driving device 38 keeps driving the table top 36 as shown in FIG. 4D. When the table top 36 is moved upward to reach the height corresponding to the vertical position "S", the patient P blocks the optical path of the light from the light beam generator 32 to the light beam detector 34. Then, the light emitted from the light beam generator 32 is no longer incident on the light beam detector 34. The light beam detector 34 generates a detection signal of high level as shown in FIG. 4E, which represents the blockage of the optical path. Then, the analog switch ASW is opened, the output terminal of the operational amplifier OP2 and the capacitor C is disconnected, and the charge voltage $V_{hold}$ of the capacitor C is held constant from this moment. The charge voltage $V_{hold}$ at this moment corresponds to $(S+L)/2$; ½ the sum of the output signal H(S) from the position detector 40 corresponding to the vertical position "S" and the output signal H(L) from the position detector 40 corresponding to the central horizontal line position "L". This value $[(S+L)/2]$ provides the height at which the center of the part of body to be photographed of the patient P may be aligned with the horizontal line passing the center of the photographing region. Therefore, at the time at which the signal of high level representing the blockage of light is emitted from the light beam detector 34, the charge voltage $V_{hold}$ corresponding to $H[(S+L)/2]$ is held at the capacitor C as a reference for alignment.

The table top 36 is not yet at the position $[(S+L)/2]$ when the signal representing the blockage of light is generated by the light beam detector 34. Therefore, the signal H(X) is lower than $H[(S+L)/2]$ and the comparator OP3 generates a signal of high level which represents the misalignment of the two positions. The driving device 38 keeps driving the table top 36 upward.

When the part of body to be photographed comes to the position represented by $(S+L)/2$ in FIG. 4A, the output signal H(X) from the position detector 40 takes a value corresponding of that of $H[(S+L)/2]$ which, in turn, corresponds to the position of $(S+L)/2$. When the output signal H(X) from the position detector 40 equals $H[(S+L)/2]$, the comparator OP3 detects the coincidence of this signal $H[(S+L)/2]$ with the signal $H[(S+L)/2]$ of the capacitor C and produces a signal of low level as shown in FIG. 4G. This signal is input to the driving device 38. When this signal of low level is input, the driving device 38 stops operating and the table top 36 thus stops moving upward. In this manner, the center of the part of body is aligned with the horizontal line passing through the center of the photographic region.

According to the configuration shown in FIG. 3, the power source must be included so that the operational amplifiers OP1 and OP2 and the comparator OP3 of the controller 44 may be set at suitable potentials to be rendered operative when the system operation switch 42 is turned on. However, since this is not the essential requirement of the present invention and the connections for this purpose may be easily understood by a skilled in the art, it is omitted from the drawings for the sake of simplicity. Furthermore, in order to render the switch 42 operative upon turning the light beam generator 32 and the position detector 40 on, switches which may be turned on with the on state of the switch 42 must be incorporated respectively between the potential V1 and the resistor Rn, and between the potential V1 and the resistors Rp1 and Rp2. These switches are also omitted for the sake of simplicity.

For the same reason, the reset circuit, the protective circuit and so on are omitted.

As may be seen from the description of the embodiments of the present invention, in accordance with the present invention, the center of the part of body to be photographed may be automatically aligned with the position "L" of the horizontal line passing through the center of the photographing region, and the center of the part of body may be correctly set at the center of the reconstructed tomogram. Accordingly, a tomogram of higher precision may be obtained and the head of the patient is automatically positioned, so that the operability if facilitated.

With many of the conventional CT apparatus, the gantry can be inclined through a suitable angle so as to obtain a tomogram of the part of body which is inclined with respect to the longitudinal axis of the patient. In such a case, a light beam generator is incorporated for setting the inclined angle to a desired value. By adopting the light beam generator 32 as the light beam generator which is normally used for setting an inclined angle, the construction of the unit may be simplified and the manufacturing cost of the apparatus may be reduced to the minimum.

The present invention is not limited to the particular embodiments described above. For example, the automatic positioning system may be applied not only to vertical positioning but also to horizontal positioning.

If a head rest is made slightly smaller than the head of the patient, the light beam will be blocked by the profile of the head, so that the head of the patient may be set at the center of the photographing region with the unit according to the present invention. On the other hand, if the head rest is larger than the head and the light beam is blocked by the profile of the head rest, the head rest may comprise a transparent body. Then, the head of the patient may be set at the center of the photographing region with the apparatus of the present invention. The unit of the present invention is not limited to photographing a head, but may be similarly applied to photographing other body portions of a patient.

Accordingly, the present invention is not limited to the particular embodiments described above, and many changes and modifications may be made by the skilled in the art within the spirit and scope of the present invention.

What we claim is:

1. A positioning unit for a radiation tomography apparatus comprising:

light beam detection means and a light beam generator which are disposed opposite to each other on a horizontal line passing through the center of a photographing region irradiated by X-rays;

a table top on which an object is laid;

driving means for lifting and lowering said table top;

position detection means for outputting a signal whose magnitude corresponds to a positon of said table top; and controller which obtains distance data corresponding to a distance from an upper surface of a part of body to be photographed of the object to said horizontal line of said photographing region, based on an output signal of said light beam detection means and an output signal of said position detection means, which obtains distance data necessary for aligning said horizontal line of said photographing region with the center of the part of body to be photographed, from the distance data and data corresponding to said horizontal line, and which drives said driving means until an output which corresponds to the distance data is obtained from said position detection means.

2. A unit according to claim 1, wherein said controller comprises:

arithmetic means for performing an operation $(S+L)/2$ where S is a vertical position of said table top when the upper surface of the part of body reaches a position "L" of the horizontal line;

capacitive means for accumulating charge of an amount corresponding to the operation result of $(S+L)/2$;

switch means, disposed between said arithmetic means and said capacitive means, for being opened in response to a signal output from said light beam detection means when the upper surface of the part of body reaches said horizontal line position "L"; and comparator means for comparing a value $H[(S+L)/2]$ of the charge accumulated by said capacitive means with an output signal from said position detection means corresponding to said horizontal line position "L" to output a drive stop signal.

3. A unit according to claim 1, wherein said position detection means comprises:

resistor means across ends of which is applied a suitable potential difference;

a first terminal connected to a point on said resistor means corresponding to said horizontal line position "L"; and a second terminal which moves on said resistor means in cooperation with the driving operation of said driving device to obtain a potential corresponding to a position of said table top.

4. A unit according to claim 1, wherein said light beam detection means comprises a phototransistor which is turned on upon reception of a light beam from said light beam generator.

* * * * *